United States Patent [19]

Edwards

[11] 4,187,301
[45] Feb. 5, 1980

[54] 17 BETA-THIOCARBOXYLIC ACID ESTERS OF 6 ALPHA, 6 BETA-DIFLUORO-3-OXOANDROST-4-ENES

[75] Inventor: John A. Edwards, Los Altos, Calif.

[73] Assignee: Syntex (U.S.A.) Inc., Palo Alto, Calif.

[21] Appl. No.: 893,389

[22] Filed: Apr. 5, 1978

[51] Int. Cl.$^2$ .................. A61K 31/58; C07J 71/00
[52] U.S. Cl. .................. 424/241; 260/239.55 D; 424/243; 260/397.1; 260/397.45
[58] Field of Search .................. 424/241, 243; 260/397.1; /Steroids MS File

[56] References Cited

U.S. PATENT DOCUMENTS

| | | | |
|---|---|---|---|
| 3,856,828 | 12/1974 | Phillipps et al. | 260/397.1 |
| 3,989,686 | 11/1976 | Phillipps et al. | 260/397.1 |

Primary Examiner—Elbert L. Roberts
Attorney, Agent, or Firm—Tom M. Moran; Gerard A. Blaufarb

[57] ABSTRACT

Certain 3-oxoandrost-4-ene and 3-oxoandrosta-1,4-diene 17 beta-thiocarboxylic acid esters substituted at the 6 alpha, 6 beta-positions with fluorine substituents are useful as anti-inflammatory steroids. These compounds are optionally substituted at the 9 alpha position with fluoro, chloro or bromo; substituted at the 11 with a keto-, a beta-hydroxy or a beta-chloro (the latter only when there is a 9 alpha-chloro); substituted at 16 alpha, 17 alpha-positions with isopropylidenedioxy; and substituted at 16 alpha (or 16 beta) with methyl or hydrogen when there is a 17 alpha-hydroxy (or an ester).

21 Claims, 6 Drawing Figures

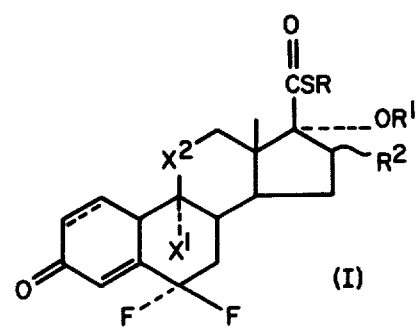
(I)
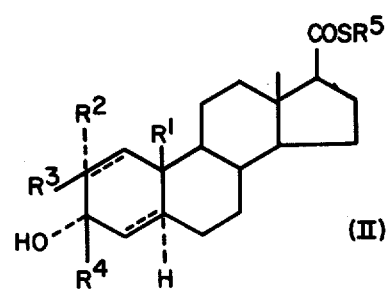
(II)

U.S. Patent Feb. 5, 1980 Sheet 2 of 6 4,187,301
REACTION SEQUENCE A
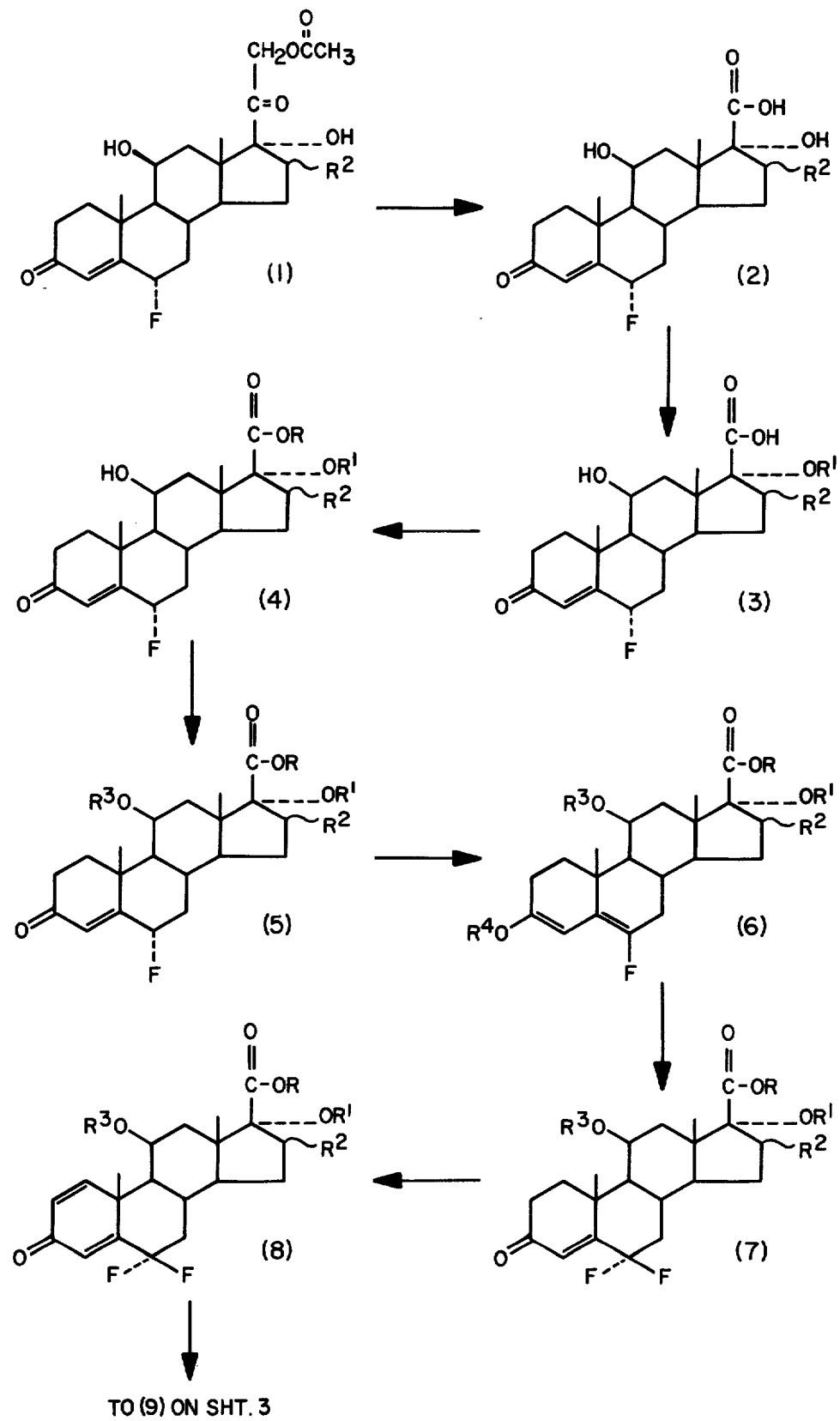
TO (9) ON SHT. 3

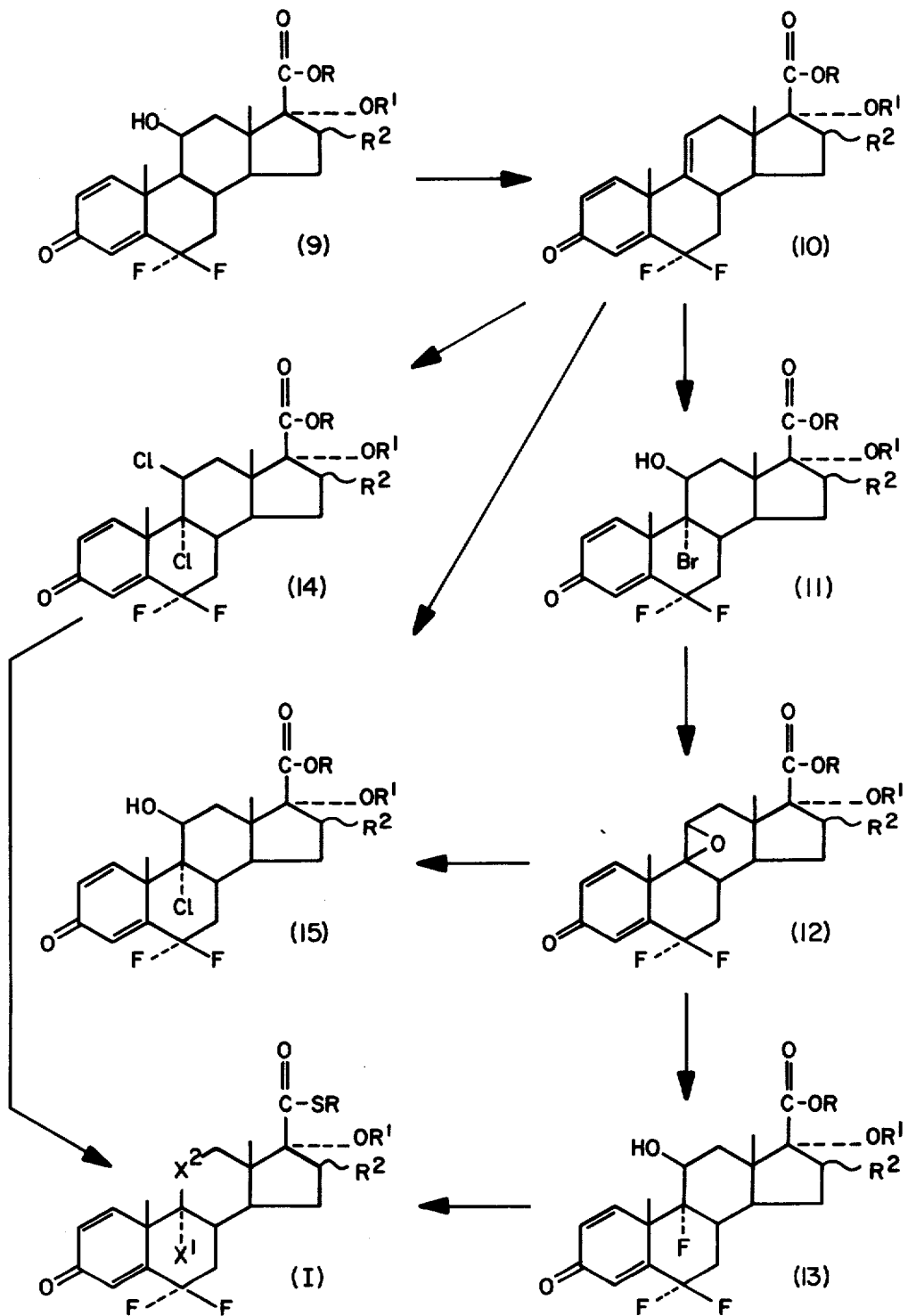

REACTION SEQUENCE B
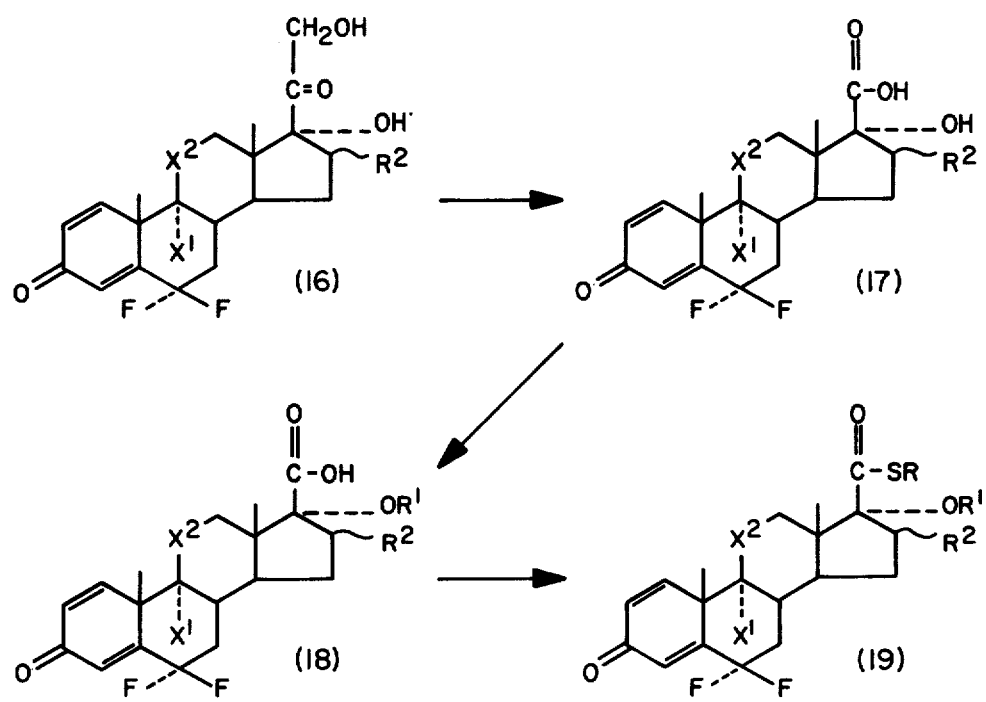

REACTION SEQUENCE C
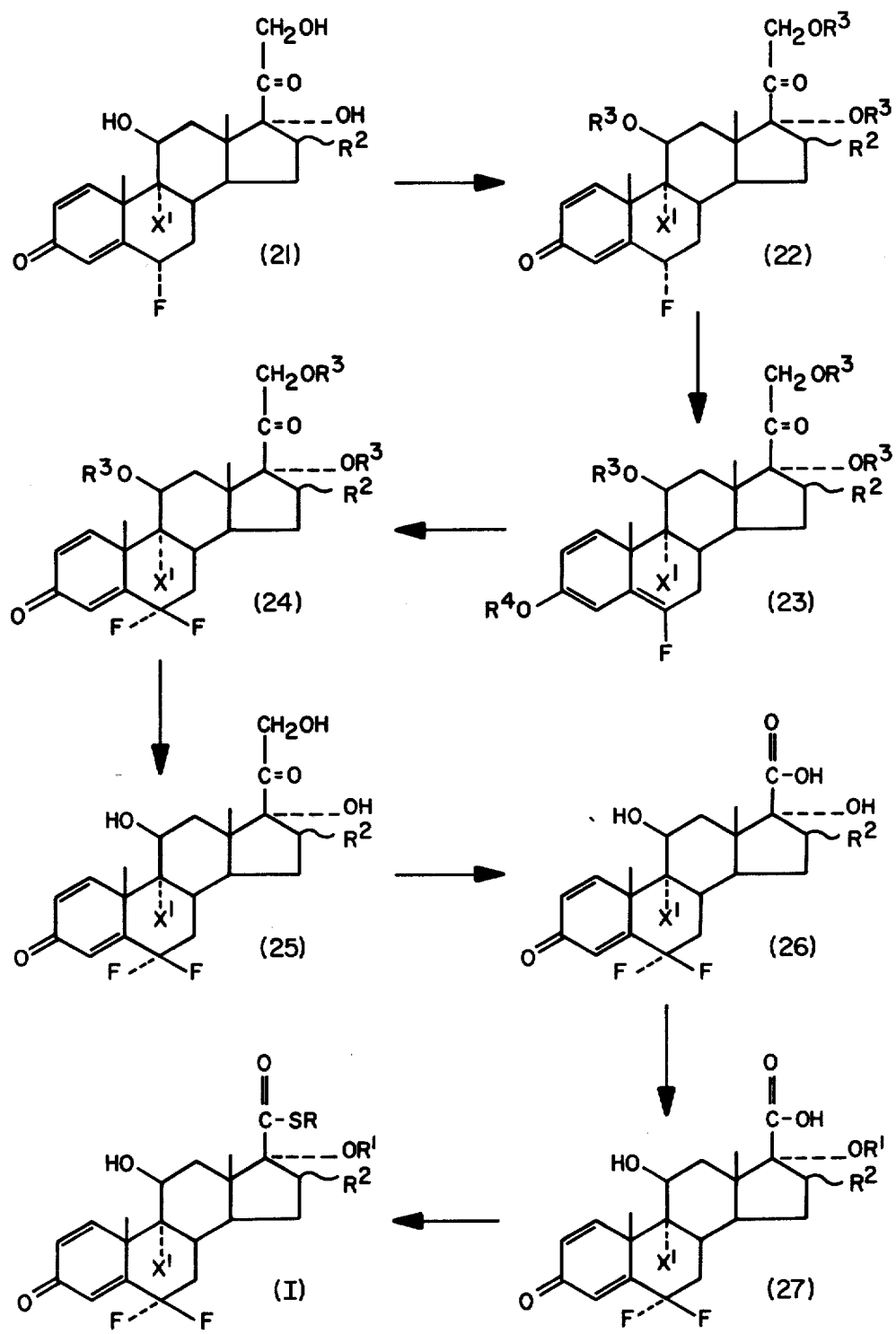

REACTION SEQUENCE D
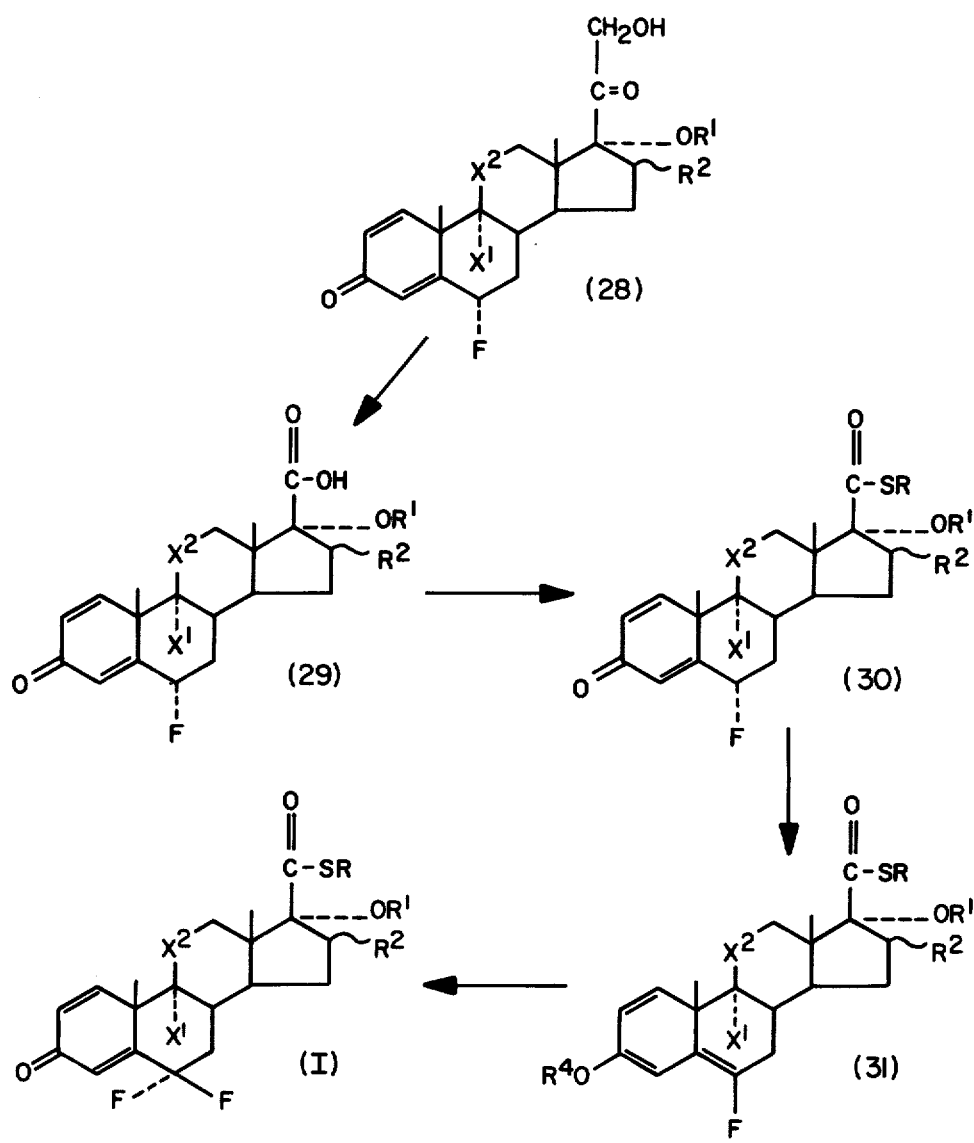

17 BETA-THIOCARBOXYLIC ACID ESTERS OF 6 ALPHA, 6 BETA-DIFLUORO-3-OXOANDROST-4-ENES

BACKGROUND OF THE INVENTION

1. Field of the Invention

This invention relates to novel derivatives of alkyl, phenyl or benzyl 3-oxoandrost-4-ene 17 beta-thiocarboxylates and the corresponding androsta-1,4-dienes. More specifically, it relates to anti-inflammatory 16 alpha,17 alpha-acetonides and 17 alpha-hydroxy-16 alpha-methyl compounds which are substituted at the 6 alpha and 6 beta positions with fluorine substituents. The invention further relates to pharmaceutical anti-inflammatory compositions comprising a selected compound of the invention in combination with pharmaceutically acceptable excipient.

2. Prior Art

Certain 3-oxoandrost-4-ene 17 beta-carboxylic acids which are substituted at the 9 position with chlorine or fluorine and at the 11 position with keto or hydroxy or chloro group are known. See for example U.S. Pat. No. 3,828,080. It is also known that 3-oxoandrost-4-ene 17 beta-carboxylic acids may be substituted at both the 9 alpha and 6 alpha positions with fluoros. See for example U.S. Pat. No. 3,636,010.

It is also known from U.S. Pat. No. 3,989,686 to Phillipps et al of Glaxo that steroids of formula (II) wherein $R^1$ is H or $CH_3$;
$R^2$ is H or $CH_3$;
$R^3$ is H or, when $R^2$ is H, $C_{1-6}$ alkoxy, $C_{1-5}$ alkyl, thiocyanato or halogen;
$R^4$ is H or $CH_3$;
$R^5$ is $C_{1-6}$ alkyl optionally substituted by halo or $NR^6R^7$, where $R^6$ and $R^7$ are the same or different $C_{1-6}$ alkyl or $R^6$ and $R^7$ together with N are morpholino, thiamorpholino or morpholino substituted with $C_{1-6}$ alkyl; and
the dotted line in the "A" ring represent an optional double bond at these positions. These compounds are useful as anesthetics.

Methyl 3 beta-acetoxyallothiolcholonate and methyl 3 beta-acetoxy-etiothiochol-5-enate are also known. See, e.g., Jerger et al, Helv. Chem. Acta. 29, 684–92 (1947).

A heretofore unknown series of 3-oxo-androst-4-ene 17 beta-thiocarboxylates and derivatives thereof being substituted at the 6 alpha and 6 beta positions with fluoro has been discovered and is disclosed herein. The 17 beta-carboxylates exhibit good anti-inflammatory activity and few adverse side effects.

SUMMARY OF THE INVENTION

One aspect of this invention is a compound chosen from those represented by the formula (I) wherein $X^1$ is hydrogen, fluoro, chloro or bromo;
$X^2$ is $=C=O$ or

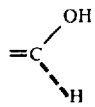

or is

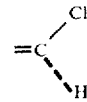

when $X^1$ is chloro;
R is alkyl of 1 through 6 carbon atoms or is phenyl or benzyl optionally substituted with a substituent which is alkyl of 1 through 4 carbon atoms, alkoxy of 1 through 4 carbon atoms or halo;
$R^1$ is hydrogen or alkanoyl of 2 through 6 carbon atoms when $R^2$ is hydrogen, alpha-methyl or beta-methyl;
$OR^1$ and $R^2$ together are 17 alpha,17 alpha-isopropylidenedioxy; and
the bond between C-1 and C-2 is a double or single bond.

Another aspect of this invention is an anti-inflammatory pharmaceutical composition which comprises a suitable pharmaceutical excipient in combination with an effective amount of a suitable compound chosen from those represented by Formula (I), above, wherein each of the substituents are as defined. Particularly valuable compounds in this composition are set forth hereafter.

Still another aspect of this invention is a method for treating an inflamed condition in mammals which comprises treating the afflicted mammal with an effective amount of a suitable compound chosen from those represented by formula (I), above, wherein the substituents $X^1$, $X^2$, R, $R^1$ and $R^2$ are as defined above.

Still another aspect of this invention is a process for preparing the compounds of this invention, which process comprises trating a corresponding reactive derivative of a 17 beta-carboxylic acid with an alkali metal salt of an appropriate alkyl, phenyl or benzyl sulfide (RSH).

Still another aspect of this invention is a process for preparing the compounds of this invention, which process comprises 6-fluorinating a corresponding 6-fluoro-3-alkoxyandrosta-3,5-diene 17 beta-thiocarboxylate.

BRIEF DESCRIPTION OF THE DRAWINGS

Formula (I) sets forth a general structure of the compounds of this invention.

Formula (II) sets forth a general structure of the compounds of the prior art.

Reaction Sequence A sets forth a process for preparing the compounds of this invention wherein the substituents at the 9 alpha and 11 beta positions are added as the last step prior to the formation of the 17 beta-thiocarboxylate.

Reaction Sequence B sets forth a process for preparing compounds of this invention from known 6 alpha,6 beta-difluoropregna-1,4-dienes.

Reaction Sequence C sets forth a process for preparing compounds of this invention from pregna-1,4-dienes wherein the elimination of the 21-carbon is performed as the second to last step prior to forming the 17 beta-thiocarboxylate.

Reaction Sequence D sets forth a process for preparing compounds of this invention wherein the second fluoro is added at the 6-position after a 17 beta-thiocarboxylate is formed.

DETAILED DESCRIPTION AND PREFERRED EMBODIMENTS

Compounds

In its broadest aspect, this invention is a compound chosen from those represented by formula (I) wherein
$X^1$ is hydrogen, fluoro, chloro or bromo;
$X^2$ is =C=O or

or is

when $X^1$ is chloro;
R is alkyl of 1 through 6 carbon atoms or is phenyl or benzyl optionally substituted with alkyl of 1 through 4 carbon atoms, alkoxy of 1 through 4 carbon atoms or halo;
$R^1$ is hydrogen or alkanoyl of 2 through 6 carbon atoms when $R^2$ is hydrogen, alpha-methyl or beta-methyl;
$OR^1$ and $R^2$ together are 16 alpha,17 alpha-isopropylidenedioxy; and
the bond between C-1 and C-2 is a double or single bond.

One subgroup of the broad aspect of this invention includes the compounds represented by formula (I) wherein R is benzyl, phenyl or alkyl of 1–6 carbons (preferably methyl or ethyl); $OR^1$ and $R^2$ together are 16 alpha,17 alpha-isopropylidenedioxy; $X^1$ is hydrogen, fluoro or chloro; $X^2$ is

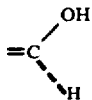

or is also

when $X^1$ is chloro. Of this subgroup the compounds wherein R is methyl and $X^1$ is fluoro or chloro are preferred.

Another subgroup of the broad aspect of the invention comprises those compounds represented by the formula (I) wherein $R^2$ is alpha-methyl; $R^1$ is alkanoyl of 2–6 carbon atoms; R is alkyl of 1–6 carbon atoms, benzyl or phenyl; $X^1$ is hydrogen, fluoro or chloro; and $X^2$ is

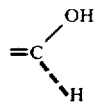

or is also

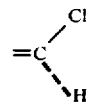

when $X^1$ is chloro. Of this subgroup, those compounds wherein R is alkyl of 1–2 carbon atoms (particularly methyl) are preferred, and particularly preferred are those wherein R is methyl; $X^1$ is fluoro or chloro; and; $X^2$ is

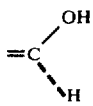

or is

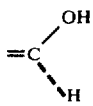

when $X^1$ is chloro.

In defining the compounds of this invention the term "alkyl" includes both straight chain and branched alkyl groups, thus "alkyl" of 1–6 carbons includes such as methyl, ethyl, n-propyl, isopropyl, n-butyl, isobutyl, t-butyl, pentyl, isoamyl, n-hexyl and the like. These alkyls are optionally substituted with a halogen atom such as fluorine, chlorine, bromine or iodine e.g. fluoromethyl, 2-chloroethyl, 3-bromopropyl, 4-bromo-n-butyl, and the like. The phenyl and benzyl substituents may be substituted on the phenyl ring at the 2, 3 or 4-positions with one substituent such as alkoxy (e.g. methoxy, ethoxy, n-propoxy, t-butoxy and the like), alkyl of 1–4 carbons (e.g. methyl, ethyl, isopropyl, n-propyl, t-butyl, n-butyl, etc.), or a halo such as fluoro, chloro, bromo or iodo. Preferably the substitution is at the 2 or 4 positions.

The term "alkanoyl" refers to a radical of the formula

wherein $R^4$ is alkyl of 1–5 carbon atoms and includes, e.g., acetyl, propionyl, butyryl, valeryl, caproyl and the like.

In naming the compounds of this invention the substituents present on the androstane ring shall be included alphabetically and the compounds shall be alkyl (or phenyl or benzyl) 17 beta-carboxylates. For example, if in formula (I), above, $X^1$ is chloro, $X^2$ is

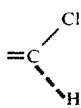

R is methyl, R¹ is acetoxy and R² is alpha-methyl the name is methyl 17 alpha-acetoxy-9 alpha,11 beta-dichloro-6 alpha,6 beta-difluoro-16 alpha-methyl-3-oxoandrosta-1,4-diene-17 beta thiocarboxylate. If on the other hand, R is hydrogen but X¹, X², X³, X⁴, R¹ and R² are the same the compound is named 17 alpha-acetoxy-9 alpha,11 beta-dichloro-6 alpha,6 beta-difluoro-16 alpha-methyl-3-oxoandrosta-1,4-diene 17 beta-thiocarboxylic acid.

Compound Preparation

The compounds of the invention may be prepared by any convenient method and in most cases they can be prepared by conventional techniques. They may, for example, be prepared by reacting a reactive derivative of an appropriate androsta-1,4-diene 17 beta-carboxylic acid (or the corresponding 4-ene) with an excess (e.g., about 1.05 to about 5 molar equivalents based on the steroid) an of alkali metal salt of a compound of the formula RSH where R is alkyl, benzyl or phenyl. Representative alkali metal salts include sodium methyl sulfide, sodium ethyl sulfide, sodium benzyl sulfide, sodium phenyl sulfide, potassium methyl sulfide, and the like. The alkali metal salt can be reacted directly with the reactive derivative of the 17 beta-carboxylic acid, or the salt can be formed in situ by mixing an alkali metal hydride, such as sodium hydride or potassium hydride, with an alkyl, phenyl or benzyl sulfide. The thioesterification reaction readily takes place at temperatures of about 10° to 100° C. (preferably at ambient temperatures of about 20°-25° C.) in a suitable insert solvent such as dimethylformamide, diethylformamide, dimethylacetamide, and the like.

The reaction derivative of the 17 beta-carboxylic acid may be an acid chloride, but is preferably a mixed anhydride, such as the dialkyl phosphate ester prepared by reacting a dialkyl (1–4 carbons) chlorophosphate (e.g. diethyl chlorophosphate) with the appropriate 17 beta-carboxylic acid in an inert solvent such as tetrahydrofuran (THF) under an inert atmosphere (nitrogen) at temperatures of about 10°-50° C., preferably about 20°-25° C.

Several overall processes maybe employed to prepare the compounds of this invention from known pregnanes. These are outlined in Reaction Sequences A-D.

Reaction sequence (A) sets forth essentially a three-part process which is applicable to steroids having a 16 alpha, 17 alpha, acetonide or 17 alpha-hydroxy-16 methyl substituents. One part is to eliminate the 21 carbon atom from a suitable 21-hydroxy-6 alpha-fluoro pregnane, or a suitable ester thereof, the other part is to fluorinate, at the 6 beta-position, and the third part is the formation of the 17 beta-thiocarboxylate. The fluorination is represented as a two step process, the elimination of the 21-carbon atom is essentially a one step process, the 17 beta-thiocarboxylate is represented as a one step process, and the other steps are performed to protect hydroxy or acid groups from reaction as needed. In this Reaction Sequence, R is a suitable alkyl of 1–6 carbon atoms, benzyl or phenyl; R¹ is alkanoyl of 2–6 carbon atoms; R² is alpha-methyl, beta-methyl or hydrogen; R³ is alkanoyl of 2–6 carbons; and R⁴ is methyl or ethyl.

The elimination of a 21 carbon atom from a suitable pregnane represented by formula (1) is readily accomplished by any means known in the art such as using sodium hypobromite or hypoiodite as taught in U.S. Pat. No. 2,769,822 or by using sodium periodate. Preferably, however, the elimination of the 21-carbon atoms is carried out by using an alkalil metal carbonate in alcohol in the presence of oxygen as described in PA-880, filed even date herewith. In the latter case the reaction is carried out at room temperature and atmospheric pressure while the source of oxygen is preferably air. Generally the reaction will be completed within less than 72 hours with a constant stream of air being bubbled into a stirred reaction mixture to give a compound of formula (2).

Once a compound represented by Formula (2) is obtained it is first reacted with an appropriate alkanoyl anhydride, such as propionic anhydride, acetic anhydride, butyric anhydride, caproic anhydride and the like in the presence of a suitable organic base such as triethylamine in an inert solvent. Preferably the solvent is the anhydride itself which is present in a substantial molar excess over the reactant represented by Formula (2). This results in a compound represented by Formula (3) wherein R¹ is alkanoyl of 2–6 carbon atoms. The compound is readily precipitated from the organic solvent by adding water and the precipitate is then readily filtered and dried in preparation for the next step. It will be recognized by one of skill in the art that there is a 16 alpha, 17 alpha-isopropylidenedioxy group in a compound of formula 1, this step is superfluous.

In the next step the compound represented by Formula (3) is reacted with a suitable alkyl or benzyl iodide in the presence of a suitable inert solvent such as dimethyl formamide or dimethyl acetamide along with a weak base such as sodium bicarbonate.

The resulting compound represented by Formula (4) is readily precipitated from the reaction mixture by adding water, the precipitate is filtered and air dried to afford a compound which is then reacted with an alkanoyl anhydride such as acetic anhydride in a suitable amine such as trimethyl amine in the presence of a catalytic amount of dimethylaminopyridine to form a compound represented by Formula (5) wherein R³ is alkanoyl of 2–6 carbon atoms. The reaction generally takes place at room temperature. By cooling the resulting reaction mixture to about 0° C. and diluting with water, a precipitate forms which is readily collected by filtration and air dried to give a product represented by (5) which is then used for the next step.

The 3-enol ether of formula (6) where R⁴ is methyl or ethyl is prepared by treating a compound of formula (5), with an alkyl orthoformate, preferably methyl orthoformate or ethyl orthoformate, in the presence of an acid catalyst, such as sulfuric acid, p-toluenesulfonic acid, and the like, in an inert non-aqueous, preferably anhydrous, organic solvent, e.g. methanol or ethanol, to afford a compound of formula (6) which is then isolated by conventional techniques. For example, the reaction mixture is neutralized and water is added to crystallize the enol ether derivatives. The solid is then collected by filtration.

The resulting compound of formula (6) then treated with perchloryl fluoride in a mixture of 90% acetone 10% water at room temperature to furnish the compounds of formula (7). The reaction is conducted at temperatures in the range of from about −78° C. to about room temperature, preferably starting at −78° C. and slowly allowing the mixture to warm. About 0.9–1.1 molar equivalents of perchloryl fluoride for each mole of the compound of formula (6) are utilized.

The 6,6-gem-difluoro steroids of formula (7) are isolated by conventional techniques. For example, the reaction mixture is cautiously neutralized with an aqueous basic solution and the product is precipitated by the addition of water and elimination of the acetone followed by chromatography on silica gel. The solid product is collected by filtration. The product can then be purified by dissolving an inert organic solvent, immiscible with water, as for example, a halogenated hydrocarbon, such as methylene chloride, or a water-immiscible ether, such as diethylether, washing with water to neutrality, drying and evaporating to dryness. The product can be further purified by recrystallization, chromatography, and the like.

The unsaturation at the C 1–2 double bond, is introduced into the novel compounds of formula (7) by conventional techniques to furnish the novel compounds of formula (8). For example, the novel compounds of formula (7) can be refluxed with selenium dioxide in the presence of 4-butanol and pyridine, or refluxed with selenium dioxide and chlorobenzene, or refluxed with 2,3-dichloro-4,6-dicyano-1,4-benzoquinone in dioxide in the presence of catalytic amounts of p-toluene sulfuric acid to afford a compound of formula (8).

The compound represented by Formula (8) is thereafter hydrolyzed by mixing it with a suitable solvent such as methanol and stirring with a one molar solution of a strong base such as sodium or potassium hydroxide (anhydrous) until the acetyl portion $R^3$ is hydrolyzed to form a compound represented by formlula (9). The reaction mixture is acidified with a suitable organic acid such as glacial acetic acid and concentrated under reduced pressure to a small volume. Water is added while methanol is continuatlly removed under pressure. The residue is extracted from the aqueous mixture with dichloromethane to give a solution which is then dried with sodium sulfate, filtered and the dichloromethane is removed under pressure to give a product represented by formula (9).

The compound so prepared is then reacted at low temperatures of about 0°–10° C. with thionyl chloride and anhydrous pyrridine. The thionyl chloride is added slowly to the pyrridine/compound (9) mixture to give a compound represented by formula (10) which has a double bond between carbons 9 and 11. Alternatively, the 11 hydroxy steroid of compound (9) may be treated with methane sulfinyl chloride in dimethyl formamide or dichloromethane in the presence of pyrridine containing a catalytic amount of sulfur trioxide (about 5% as compared to the steroid). The desired steroid having double bond at 9–11 is precipitated from the reaction mixture by slowly adding water at low temperatures such as 0° to 10° C. until a precipitate is formed which is then collected by filtration water, washed and dried.

The 9 alpha,11 beta-fluorhydrin (13); 9 alpha,11 beta-chlorhydrin (15); 9 alpha,11 beta-bromhydrin (11) and 9 alpha,11 beta-dichloro compounds are readily prepared from the compound of formula (10) by methods known in the art. The 9 alpha,11 beta-bromhydrin is prepared by treating the compound of formula (10) with N-bromo acetamide and perchloric acid in dioxane or tetrahydrofuran. The resulting 9-bromo-11-hydroxy steroid (11) is refluxed with sodium hydroxide in methanol to give a 9 beta,11 beta-oxido steroid represented by formula (12). This in turn is treated with hydrogen chloride or hydrogen fluoride in an inert, nonaqueous, preferably anhydrous, solvent or mixture of such solvents. For example, see U.S. Pat. No. 3,211,758 to Tarkoey wherein a hydrogen fluoride/urea complex is employed. The 9 alpha,11 beta-dichloro compound (14) is prepared by treating the corresponding 9(11)-pregnene with chlorine gas in chloroform in the presence of pyridine at 0° to room temperature. The resulting compounds represented by formulas (11), (14), (13) and (15) are readily converted to a reactive derivative of the 17 beta-carboxylic acids and thioesterified as discussed hereinbefore.

Alternatively the compounds of the invention may be prepared according to the reaction sequence (B) starting from known 6 alpha,6 beta-difluoro-21-hydroxy-pregna-1,4-dienes. The compound represented by formula (16) are known in the art as taught in U.S. Pat. No. 3,546,215 to Fried. The 21 carbon is eliminated from the compound represented by formula (16) by methods discussed hereinbefore. The resulting compound represented by formula (17) is esterified to form a compound represented by formula (18) as discussed hereinbefore with regard to a compound of formula (3). This is then thioesterified to form a compound by formula (19) as discussed hereinbefore.

In Reaction Sequence (C) the 21-carbon atom is not removed until the third to the last step; however, the reaction conditions for preparing the intermediates are similar to analagous reactions discussed for Reaction Sequences (A) and (B) hereinbefore.

In the first step of Reaction Sequence (C), a compound of formula (21) is converted into a compound of formula (22) by reacting the former with a suitable anhydride such as acetic anhydride with ethyl amine and dimethylaminopyridine under conditions discussed in regard to converting a compound of formula (4) to (5) in Reaction Squence (A). The next two steps, i.e. fluorination of compound (22) to form compound (24) are essentially the same as discussed for fluorinating compound (5) to form a compound of formula (7) in Reaction Sequence (A). The hydrolysis of the compound of formula (24) takes place using a suitable base such as sodium bicarbonate in methanol at room temperature to form compound (25) which, in turn, is treated by methods discussed above to remove the 21-carbon and form the 17 beta-carboxylic acid (26). The corresponding 17 alpha-alkanoate (27) is formed by reacting with an appropriate anhydride. This is then thioesterified in accordance with the general principles discussed hereinbefore.

In Reaction Sequence (D), a known 21-hydroxy pregna-1,4-diene of formula (28) is treated in accordance with principles set forth hereinbefore to eliminate the 21-carbon and form a compound of formula (29). This, in turn, is thioesterified as discussed above to give a compound of formula (30) which is then reacted with triethylorthoformate or trimethylorthoformate to yield a compound represented by formula (31). This compound is then treated with perchloryl fluoride to give a compound of this invention represented by formula (I).

It will be apparent to one of skill in the art that Reaction Sequences A—D have equal applicability for preparing compounds having 16 alpha, 17 alpha-isopropylidenedioxy substituents and 17 alpha-alkanoyl-16-methyl substituents.

Suitable 21-hydroxy-3,20-dioxopregn-4-enes or pregna-1,4-dienes which useful as starting materials in Reaction Sequences (A)–(D) include known compounds such as corticosterone, hydrocortisone, prednisolone, betamethasone, dexamethasone, paramethasone, fluocinolone acetonide, triamcinolone acetonide, and the like.

A 16 methyl group is introduced by treating the corresponding 20-keto-pregn-16-ene with methyl magnesium bromide in the presence of cuprous chloride in an ether such as tetrahydrofuran. The 20-keto-pregn-16-ene is prepared by preparing the 3,20-bis-semicarbazone of a 3,20-diketo-17 alpha-hydroxy steroid, treating it with glacial acetic acid and acetic anhydride and then allowing the resulting product to react with aqueous pyruvic acid.

The 17 alpha-hydroxy group is introduced in conjunction with 16 beta-methyl group by first treating the corresponding 16-methyl-pregn-16-ene (which is prepared by treating the corresponding pregn-16-ene with diazomethane and then heating the resulting product to 180° C.) with hydrogen peroxide, in an aqueous basic media, then permitting the resulting 16,17-oxido-16-methyl steroid to react with hydrogen bromide in glacial acetic acid. The resulting 16,17-bromohydrin is hydrogenated with the use of a palladium catalyst to afford the corresponding 16 beta-methyl-17-alpha-hydroxy derivative.

The 17-alpha-hydroxy group is introduced in conjunction with the 16 alpha-methyl by methods known in the art, such as the method described by Edwards et al in the Journal of the American Chemical Society 82, 2318–22, 1960. In this process an appropriate 21-substituted-16 alpha-methylpregna-1,4-diene-3,2-dione is converted to a 21-enol acetate by refluxing with acetic anhydride and freshly distilled acetyl chloride. The 20-enol acetate is recovered and reacted with monoperphthalic acid in ether and benzene to form the 17,20-epoxide which in turn is treated with methanol and aqueous potassium hydroxide to give the 16 alpha-methyl-17 alpha-hydroxy steroid which is isolated by means known in the art.

Administration and Formulation

The compounds of this invention are useful for the relief of inflamed conditions in mammals, and more specifically are useful for relieving inflammatory manifestations or corticosteroid responsive dermatoses. Initial approximation of anti-inflammatory activity is done by the following procedure of McKenzie, S. W. and Stoughton, R. B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of the novel steroids of this invention, that is an amount which results in improvement of the inflamed conditions. Preferably the steroids are first formulated to prepare a suitable pharmaceutical formulation, as discussed hereinafter, which is then placed in contact with the afflicted area. An effective amount will depend upon the particular condition and the animal receiving the treatment but will vary between 0.001% to 10% by weight of the pharmaceutical composition and preferably will be between 0.02 and 1% by weight of the formulation. Using these levels in the formulation, a therapeutically effective and non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the animal's system.

The novel steroids of this invention may be formulated with suitable pharmaceutical excipients known in the art to form particularly effective anti-inflammatory compositions which may be administered orally, nasally, rectally, or preferably, topically. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| Water/glycol mixture (15% or more glycol) | 50–99 parts by weight |
|---|---|
| Fatty alcohol | 1–20 |
| Non-ionic Surfactant | 0–10 |
| Mineral oil | 0–10 |
| Typical pharmaceutical adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| Active Ingredients | 40–94 parts by weight |
|---|---|
| Mineral Oil | 5–20 |
| Glycol solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001–10.0 parts by weight |
|---|---|
| Propylene carbonate | 1–10 |
| Solvent | 1–10 |
| Surfactant | 1–10 |
| White Petrolatum | 70–97 | surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| Glycol solvent | 50–35 parts by weight |
|---|---|
| Fatty alcohol | 15–45 |
| Compatible plasticizer | 0–15 |
| Compatible coupling Agent | 0–15 |
| Penetrant | 0–20 |
| Active Ingredients | 0.001–10.0 |

Preparation 1

This Preparation sets forth a process for preparing 17 alpha-alkanoyloxy-6 alpha,6 beta,9 alpha-trifluoro-11 beta-hydroxy-16 alpha-methyl-3-oxoandrost-4-ene 17 beta-carboxylic acids according to Reaction Sequence (C).

A. Ten grams (10 g) of flumethasone is treated at room temperature with 20 ml of triethylamine (TEA) and 20 ml of acetic anhydride plus 2.2 g of dimethylaminopyridine. The mixture is heated on the steam bath for 5 hours. Examination of the reaction mixture by thin layer chromatography (TLC) analysis in 10% ethyl acetate/90% dichloromethane (DCM) shows the reaction to be complete. The mixture is cooled in an ice water bath, and slowly diluted with water up to a final volume of 2 liters. The semicrystalline precipitate so obtained is collected by filtration, washed with water, and dissolved in 200 ml. of DCM, dried over anhydrous sodium sulfate, filtered and concentrated to dryness. The residue is dissolved in 200 ml DCM and filtered through a column of 100 g of silica gel eluting first with 100% DCM, then 2% EtOAc/DCM, 4% EtOAc/DCM. The homogeneous fractions containing 11 beta,-17 alpha,21-triacetoxy-6 alpha,9 alpha-difluoro-16 alpha-methylpregna-1,4-diene-3,20-dione are combined and concentrated to dryness. The residue is crystallized from methanol/water to give 11 beta,17 alpha,21-triacetoxy-6 alpha,9 alpha-difluoro-16 alpha-methylpregna-1,4-diene-3,20-dione.

Ten g of the triacetate prepared in this manner is treated with 150 ml of trimethylorthoformate and 50 ml of anhydrous methanol, using 5 ml of fuming sulfuric acid as catalyst. The reaction mixture is heated at 40–50° for a period of 30 minutes, then 25 ml of TEA was added, and the mixture is concentrated under reduced pressure to dryness. The residue is dissolved in 200 ml of DCM, washed thrice with 50 ml of water; dried over anhydrous sodium sulfate, filtered, and the solvent removed under reduced pressure. The residue is dissolved in 25 mls of pyridine and treated at room temperature with 5 ml of acetic anhydride for a period of one hour. The reaction mixture is diluted slowly with 50 ml of water, stirred at room temperature for 4 hours. The precipitate so obtained is collected by filtration, washed with water, dissolved in 200 ml of DCM, dried over anhydrous sodium sulfate, filtered and concentrated to dryness. The residue is chromatographed over 100 g of silica gel in a DCM/hexane system and the homogeneous fractions are concentrated to give 7.5 g of 11 beta,17 alpha,21-triacetoxy-6,9 alphadifluoro-3-methoxy-16 alpha-methylpregna-1,3,5-triene-3-one.

A mixture of 10 g of the enol ether prepared in this manner in 300 ml of 90% acetone/10% water, is treated at room temperature with a slow stream of perchloryl fluoride for a period of 45 minutes. The reaction mixture is diluted with 300 ml of water, and the acetone is eliminated under reduced pressure. The precipitate so obtained is extracted with DCM, washed thrice with 50 ml of water, dried over anhydrous sodium sulfate, and concentrated to dryness under reduced pressure. The residue is percolated through a column of 100 g silica gel eluting with a DCM/hexane system; increasing the polarity of the eluant to 100% DCM gradually. The polarity of the eluant is increased to 1, 2 and 3% ethyl acetate in DCM. In this manner, 11 beta,17 alpha,21-triacetoxy-6 alpha,6 beta,9 alpha-trifluoro-16 alpha-methylpregna-1,4-diene-3,20-dione is eluted along with some polar impurities. The eluates are concentrated to dryness under reduced pressure. The residue is chromatographed again in 20 g of silica gel, eluting with 100% DCM first, then increasing the polarity of the eluant to 1, 2 and 3% EtOAc in DCM. The homogeneous fractions containing 11 beta,17 alpha,21-triacetoxy-6 alpha,6 beta,9 alpha-trifluoro-16 alpha-methylpregna-1,4-diene-3,20-dione are combined, concentrated to dryness, and the residue crystallized from DCM/methanol. The DCM is eliminated by evaporation to give 500 mgs of 11 beta,17 alpha,21-triacetoxy-6 alpha,6 beta,9 alpha-trifluoro-16 alpha-methylpregna-1,4-diene-3,20-dione.

Ten g of 11 beta,17 alpha,21-triacetoxy-6 alpha,6 beta,9 alpha-trifluoro-16 alpha-methylpregna-1,4-diene-3,20-dione prepared in this manner in 300 mls of methanol is treated at room temperature with 2 g of anhydrous potassium carbonate under N$_2$ for 1 hour. The mixture is acidified by addition of 10 ml of glacial acetic acid, diluted with 300 mls of water, and the methanol eliminated under reduced pressure, to leave a crystalline precipitate of 6 alpha,6 beta,9 alpha-trifluoro-11 beta,17 alpha,21-trihydroxy-16 alpha-methylpregna-1,4-diene-3,20-dione.

Ten g of 6 alpha,6 beta,9 alpha-trifluoro-11 beta,17 8 alpha,21-trihydroxy-16 alpha-methylpregna-1,4-diene-3,20-dione, prepared in this manner, in 300 ml of anhydrous methanol is treated with 30 g of anhydrous potassium carbonate at room temperature under stirring for a period of 24 hours while a continuous current of air is bubbled through the reaction mixture. Methanol is added at intervals to maintain the original volume. The reaction mixture is diluted with 300 mls of water, and then acidified with concentrated hydrochloric acid until a pH of 2 was reached. The reaction mixture is concentrated under reduced pressure, until most of the methanol is eliminated. The mixture is cooled to room temperature, and the resulting crystalline precipitate is collected by filtration, water washed, and air dried to yield 6 alpha,6 beta,9 alpha-trifluoro-11 beta,17 alpha-dihydroxy-16 alpha-methyl-3-oxoandrosta-1,4-diene 17 beta-carboxylic acid.

Ten g of 6 alpha,6 beta,9 alpha-trifluoro-11 beta,17 alpha-dihydroxy-16 alpha-methyl-3-oxoandrosta-1,4-diene 17 beta-carboxylic acid prepared in this manner are treated at room temperature with 50 ml of propionic anhydride and 50 mls of anhydrous pyridine. The mixture is stirred for one hour, and then slowly diluted with water up to 2 liters while the mixture is cooled in an ice-water bath. The crystalline precipitate so obtained is collected by filtration, washed with water and air dried, to give 6 alpha,6 beta,9 alpha-trifluoro-11 beta-hydroxy-16 alpha-methyl-3-oxo-17 alpha-propionyloxy-androsta-1,4-diene 17 beta-carboxylic acid.

Preparation 2

By following in principle the procedure set forth in Preparation 1, Part A but substituting fluocinolone acetonide for flumethasone, one obtains 6 alpha,6 beta,9 alpha-trifluoro-11 beta-bydroxy-16 alpha,17 alpha-isopropylidenedioxy-3-oxoandrosta-1,4-diene 17 beta-carboxylic acid.

It will be appreciated by one of skill in the art that the last reactive step in Part A of Preparation 1 will not be performed because there is no 17 alpha-hydroxy.

Preparation 3

A process is set forth for preparing alkyl, benzyl or phenyl 17 alpha-alkanoyloxy-16 alpha-methyl-3-oxoandrosta-1,4-diene 17 beta-thiocarboxylates which are substituted with hydrogen, fluoro or chloro at the 6 alpha-position; with fluoro, chloro, bromo or hydrogen at the 9 alpha-position; and 11 beta-hydroxy or 11 beta-chloro when there is a chloro at 9 alpha.

A. Preparation of methyl 6 alpha,9 alpha-difluoro-11 beta-hydroxy-16 alpha-methyl-3-oxo-17-propionyloxyandrosta-1,4-diene 17 beta-thiocarboxylate.

Thirty-five grams of flumethasone are mixed with 550 ml of methanol and 35 g of anhydrous potassium carbonate and stirred at room temperature and atmospheric pressure while a current of air is slowly bubbled through the solution for 22 hours. Methanol is added at intervals to maintain a constant volume. The reaction mixture is diluted with water to 1.5 l, then concentrated hydrochloric acid is added slowly to the mixture under magnetic stirring until a final pH of 2 is obtained. Methanol is eliminated under reduced pressure, and the resulting crystalline precipitate is collected by filtration, washed with water, and air dried to give 6 alpha, 9 alpha-difluoro-11 beta, 17 alpha-dihydroxy-16 alpha-methyl-3-oxoandrosta-1,4-diene-17 beta-carboxylic acid, melting point (m.p.) 289.5°–290° C.

Six hundred (600) mg of 6 alpha, 9 alpha-difluoro-11 beta-hydroxy-16 alpha-methyl-3-oxo-17-propionyloxyandrosta-1,4-diene 17 beta-carboxylic acid, (prepared by reacting propionic anhydride in pyridine as discussed in Preparation 1, A), are mixed with 8 ml THF and 0.2 ml triethylamine (TEA) in a suitable reaction vessel and stirred at room temperature under nitrogen. Thereafter, 0.24 g of diethyl chlorophosphate (DCP: $(C_2H_5O)_2P(O)Cl$) in 8 ml THF is added over 13 minutes. Stirring is continued for about 6 hours (pH 6). Then, 0.04 ml TEA is added followed by 0.05 gm DCP in 3 ml THF. Stirring is continued for another 17.5 hours. The resulting precipitate is filtered, washed with 10 ml THF and the filtrates are combined. To the filtrates is then added 2.05 ml of a solution prepared previously with consists of 20 ml dimethylformamide (DMF), 0.758 g 75% sodium hydride and 0.86 g (1 ml) methyl sulfide. The resulting reaction mixture of the filtrates and the DMF solution is stirred for about 5.5 hours whereupon an additional 1 ml of the DMF solution is added and stirring is continued for another 1.5 hours.

The reaction mixture is then poured into 200 ml of ethyl acetate (EtOAc) which, in turn, is washed twice with 200 ml portions of water, washed with brine, dried for about 15 hours over sodium sulfate and filtered. The solvents are then removed under reduced pressure using a rotary evaporator to give 235 mg of residue which is recystallized from acetone/hexane to give 54.3 mg of methyl 6 alpha, 9 alpha-difluoro-11 beta-hydroxy-16 alpha-methyl-17 alpha-propionyloxyandrosta-1,4-diene 17 beta-thiocarboxylate, m.p. 305°–308° C. (with decomposition).

B. By following in principle the procedure of Part A of this example but substituting other sulfides such as ethyl sulfide, isopropyl sulfide, n-butyl sulfide, phenyl sulfide, or benzyl sulfide for methyl sulfide other compounds of this invention are prepared as disclosed in PA-890, filed even date herewith, said disclosure being incorporated herein by reference.

Preparation 4

A process is set forth for preparing alkyl, benzyl or phenyl 16 alpha, 17 alpha-isopropylidenedioxy-3-oxoandrosta-1,4-diene 17 beta-thiocarboxylates of this invention which are substituted with hydrogen, fluoro or chloro at the 6 alpha-position; with hydrogen, fluoro, chloro or bromo at the 9 alpha-position; and with hydroxy at the 11 beta-position or also chloro at the 11 beta-position when there is a chloro at the 9 alpha position.

A. Methyl 6 alpha, 9 alpha-difluoro-11 beta-hydroxy-16 alpha, 17 alpha-isopropylidenedioxy-3-oxoandrosta-1,4-diene 17 beta-thiocarboxylate is prepared by following in principle the process of Preparation 3, Part A.

B. By following the procedure of Preparation 3, Part B, other suitable alkyl, phenyl or benzyl 17 beta, thiocarboxylates of this invention are prepared.

Specific embodiments of the process of this invention are found in the following Examples which are given by way of illustration only and not to be interpreted as limiting the scope of the claims appended hereto.

EXAMPLE 1

This example sets forth a process for preparing an alkyl, benzyl or phenyl 17 alpha-alkanoyloxy-6 alpha,6 beta-difluoro-16 alpha-methyl-3-oxoandrosta-1,4-diene 17 beta-thiocarboxylate of this invention represented by formula (I), above, wherein $X^1$ is fluoro, chloro, bromo or hydrogen and $X^2$ is hydroxy or is chloro.

A. Six hundred (600) mg of 6 alpha,6 beta,9 alpha-trifluoro-11 beta-hydroxy-16 alpha-methyl-3-oxo-17 alpha-propionyloxyandrosta-1,4-diene 17 beta-carboxylic acid (prepared as set forth in Part A of Preparation 1,) 8 milliliters (ml) of tetrahydrofuran (THF) and 0.2 ml triethylamine (TEA) are placed in a suitable reaction vessel. The mixture is stirred at room temperature under nitrogen and 0.24 mg of diethyl chlorophosphate (DCP) in 8 ml of THF is added thereto. The reaction mixture is stirred under nitrogen at room temperature for six hours whereupon 0.04 ml of TEA is added follwed by 0.5 mg DCP in 3 ml of THF. The resulting precipitate is filtered off and washed with 10 ml of THF.

Two and five hundredths (2.05) ml of a solution consisting of 20 ml DMF, 0.758 g 57% sodium hydride and 0.68 g methyl sulfide is added to the filtrate and the resulting mixture is stirred for 7 hours.

The resulting mixture is poured into 200 ml ethyl acetate, washed twice with 200 ml water, washed with brine, dried over sodium sulfate, filtered, and the solvents removed by rotary evaporator to yield a crude solid which is purified by recrystallizing with acetone/hexane to give methyl 6 alpha, 6 beta, 9 alpha-trifluoro-11 beta-hydroxy-16 alpha-methyl-3-oxo-17 alpha-propionyloxyandrosta-1,4-diene 17 beta-thiocarboxylate, melting point (mp) 160° C., [alpha]$_D$ −49° (Chloroform).

B. Similarly, by following the procedure of Part A of this example but substituting other starting materials prepared according to methods set forth hereinbefore for 6 alpha, 6 beta, 9alpha-trifluoro-11 beta-hydroxy-16 alpha-methyl-3-oxo-17 alpha-propionyloxyandrosta-1,4-diene 17 beta-carboxylic acid and other alkyl, benzyl or phenyl sulfides for methyl sulfide, other compounds of this invention are prepared, such as methyl 9 alpha-chloro-6 alpha, 6 beta-difluoro-11 beta-hydroxy-16 alpha-methyl-3-oxo-17 alpha-propionyloxyandrosta-1,4-diene 17 beta-thiocarboxylate;

ethyl 9 alpha-chloro-6 alpha, 6 beta-difluoro-11 beta-hydroxy-16 alpha-methyl-3-oxo-17 alpha-propionyloxyandrosta-1,4-diene 17 beta-thiocarboxylate;

ethyl 17 alpha-acetoxy-6 alpha, 6 beta,9 alpha-trifluoro-11 beta-hydroxy-16 alpha-methyl-3-oxoandrosta-1,4-diene 17 beta-thiocarboxylate;

methyl 9 alpha, 11 beta-dichloro-6 alpha,6 beta-difluoro-16 alpha-methyl-3-oxo-17 alpha-propionyloxyandrosta-1,4-diene 17 beta-thiocarboxylate;

methyl 9 alpha-bromo-6 alpha,6 beta-difluoro-11 beta-hydroxy-16 alpha-methyl-3-oxo-17 alpha-propionyloxyandrosta-1,4-diene 17 beta-thiocarboxylate;

methyl 6 alpha,6 beta-difluoro-11 beta-hydroxy-16 alpha-methyl-3-oxo-17 alpha-propionyloxyandrosta-1,4-diene 17 beta-thiocarboxylate;

ethyl 19 alpha, 11 beta-dichloro-6-alpha,6 beta-difluoro-16 alpha-methyl-3-oxo-17 alpha-propionyloxyandrosta-1,4-diene 17 beta-thiocarboxylate;

benzyl 17 alpha-acetoxy-6 alpha,6 beta,9 alpha-trifluoro-11 beta-hydroxy-16 alpha-methyl-3-oxoandrosta-1,4-diene 17 beta-thiocarboxylate; and the like.

EXAMPLE 2

This example sets forth a method for preparing alkyl, benzyl or phenyl 6 alpha,6 beta-difluoro-11 beta-hydroxy-16 alpha,17 alpha-isopropylidenedioxy-3-oxoandrosta-1,4-diene 17 beta-thiocarboxylates of formula (I) wherein $X^1$ is fluoro, chloro, bromo or hydrogen and $X^2$ is hydroxy or may be chloro when $X^1$ is chloro.

By substituting the appropriate 16 alpha,17 alpha-acetonide steroid for 6 alpha,6 beta,9 alpha-trifluoro-11 beta-hydroxy-16 alpha-methyl-3-oxo-17 alpha-propionyloxyandrosta-1,4-diene 17 beta-carboxylic acid in Part A of Example 1 and following in principle the procedure set forth therein, 16 alpha,17 alpha-acetonide steroids of this invention are prepared such as methyl 6 alpha,6 beta,9 alpha-trifluoro-11 beta-hydroxy-16 alpha,17 alpha-isopropylidenedioxy-3-oxoandrosta-1,4-diene 17 beta-thiocarboxylate;

methyl 9 alpha-chloro-6 alpha,6 beta-difluoro-11 beta-hydroxy-16 alpha,17 alpha-isopropylidenedioxy-3-oxoandrosta-1,4-diene 17 beta-thiocarboxylate;

ethyl 9 alpha-chloro-6 alpha,6 beta-difluoro-11 beta-hydroxy-16 alpha,17 alpha-isopropylidenedioxy-3-oxoandrosta-1,4-diene 17 beta-thiocarboxylate;

phenyl 9 alpha,11 beta-dichloro-6-alpha,6 beta-difluoro-16 alpha,17 alpha-isopropylidenedioxy-3-oxoandrosta-1,4-diene 17 beta-thiocarboxylate;

methyl 9 alpha-bromo-6 alpha,6 beta-difluoro-11 beta-hydroxy-16 alpha,17 alpha-isopropylidenedioxy-3-oxoandrosta-1,4-diene 17 beta-thiocarboxylate;

methyl 6 alpha,6 beta-difluoro-11 beta-hydroxy-16 alpha,17 alpha-isopropylidenedioxy-3-oxo-androsta-1,4-diene 17 beta-thiocarboxylate;

methyl-9 alpha,11 beta-dichloro-6 alpha,6 beta-difluoro-11 -beta-hydroxy-16 alpha,17 alpha-isopropylidenedioxy-3-oxoandrosta-1,4-diene 17 beta-thiocarboxylate;

ethyl-6 alpha,6 beta,9 alpha-trifluoro-11 beta-hydroxy-16 alpha,17 alpha-isopropylidenedioxy-3-oxoandrosta-1,4-diene 17 beta-thiocrboxylate; and the like.

EXAMPLE 3

An alternative process for preparing compounds of this invention represented by formula (I) is outlined by Reaction Sequence (D) wherein R is alkyl, phenyl or benzyl; $R^1$ is alkanoyl when $R^2$ is alpha-methyl; $OR^1$ and $R^2$ together are 16 alpha, 17 alpha-isopropylidenedioxy; $X^1$ is hydrogen, fluoro, chloro or bromo; and $X^2$ is

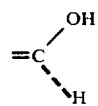

or also is

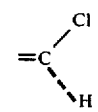

when $X^1$ is chloro.

A. Six (6) g of methyl 6 alpha, 9 alpha-difluoro-11 beta-hydroxy-16 alpha-methyl-3-oxo-17 alpha-propionyloxyandrosta-1,4-diene 17 beta-thiocarboxylate (prepared according to the process of Preparation 3) is mixed with 72 ml of trimethyl orthoformate, 24 mls of anhydrous methanol and 0.5 mls fuming sulfuric acid. The mixture is heated at 50° for 30 minutes whereupon TLC in 35% FtOAc/65% hexane, shows the reaction to be complete. Four (4) ml of TEA are added, and the solvents are eliminated under high vacuum. The residue is dissolved in 30 cc of methanol and slowly diluted with water up to 2 liters. The crystalline precipitate is collected by filtration and sucked as dry as possible to give methyl 6 alpha, 9 alpha-difluoro-11 beta-hydroxy-16 alpha-methyl-3-methoxy 17 alpha-propionyloxyandrosta-1,3-diene 17 beta-thiocarboxylate.

This material is dissolved in 300 ml of acetone/30 ml of water. Then a stream of perchloryfluoride is slowly passed through the reaction mixture for 10 minutes. TLC analysis of the reaction mixture in 35% ethyl acetate/65% hexane shows the reaction to be complete. The mixture is diluted with 100 ml of water, and the acetone is eliminated under reduced pressure. The residue is diluted up to 1 liter with water. The semicrystalline precipitate so obtained, is collected by filtration and dissolved in DCM. The water layer is extracted with DCM. The DCM layer is separated, combined with the other DCM solution and dried over anhydrous sodium sulfate and filtered. The filtrates are percolated through 20 g of silica eluting with 100% DCM. Thereafter, the column was eluted with 2% EtOAC 98% DCM to give a total volume of eluates of 4.5 l. Concentration of the eluates give 1.52 g of solid material which is then dissolved in 20 ml of DCM and is filtered trough a column of 20 g of silica gel, eluting first with DCM alone, then 0.5% EtOAC up to 3%. Non-homogeneous fractions are evaporated to give polar beta-gamma unsaturated ketone and more polar impurities. One (1) g of material which is dissolved in 20 ml methanol and 100 mg anhydrous potassium carbonate. One ml acetic acid is added and MeOH eliminated under reduced pressure to small volume and diluted up to 500 ml with water to give a crystalline precipitate wihch is filtered, dried and dissolved in 4 ml of DCM. The solution is applied to 2×2 mm 20×20 silica gel plates and developed in 35% EtOAC/65% hexane for 3 hours. Bands containing the 6,6-difluoro compound are scratched out, and the silica is extracted with DCM/EtOAC twice. Solvents are evaporated and the resiude is dissolved in small amount MeOH and precipitated with water to give 300 mg methyl 6 alpha, 6 beta, 9 alpha-trifluoro-11 beta-hydroxy-16 alpha-methyl-3-oxo-17 alpha-propionyloxyandrosta-1,4-diene 17 beta-thiocarboxylate, mp 160° C., $[alpha]_D - 49°$ (chloroform).

B. By substituting other starting materials prepared in accordance with the process of Preparations 3 and 4 for methyl 6 alpha, 9 alpha-difluoro-11 beta-hydroxy-16 alpha-methyl-3-oxo-17 alpha-propionyloxyandrosta-1,4-diene 17 beta-thiocarboxylate, other compounds of this invention are similarly prepared.

EXAMPLE 4

By following in principle the procedures set forth in Example 1 but substituting the corresponding 16 beta-methyl steroid starting material for the 16 alpha-methyl steroid starting material, the corresponding 16 beta-methyl steroids of this invention are obtained such as methyl 6 alpha,6 beta,9 alpha-trifluoro-11 beta-hydroxy-16 beta-methyl-3-oxo-17 alpha-propionyloxyandrosta-1,4-diene 17 beta-thiocarboxylate and the corresponding 17 alpha-alkanoyloxy derivatives along with other alkyl, phenyl or benzyl 17 beta-thiocarboxylates.

EXAMPLE 5

By following in principle the procedures set forth in Example 1 but substituting the corresponding 16-unsubstituted steroid starting material for the 16 alpha-methyl steroid starting material, the corresponding 16-unsubstituted steroids of this invention are obtained, such as methyl 6 alpha,6 beta,9 alpha-trifluoro-11 beta-hydroxy-3-oxo-17 alpha-propionyloxyandrosta-1,4-diene 17 beta-thiocarboxylate and the corresponding alkyl, phenyl or benzyl 17 beta-thiocarboxylates as well as the 17-alpha-alkanoyloxy derivatives.

EXAMPLE 6

This example sets forth a process for preparing an 11-keto compound by oxidizing any of the 11 beta-hydroxy steroids set forth in Preparations 1 or 2.

One g of 6-alpha,6 beta,9 alpha-trifluoro-11 beta-hydroxy-16 alpha-methyl-3-oxo-17 alpha-propionyloxyandrosta-1,4-diene 17 beta-carboxylic acid is dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 6 alpha,6 beta,9 alpha-trifluoro-16 alpha-methyl-3,11-dioxo-17-propionyloxyandrosta-1,4-diene-17 beta-carboxylic acid. This is then reacted according to the process of Example 1 to give a compound of the invention.

EXAMPLE 7

This process sets forth a process for converting androsta-1,4-diene 17 beta-carboxylic acids and their derivatives to the corresponding androst-4-ene 17 beta-carboxylic acids and the respective derivatives.

A solution of 25 mg of tris-(triphenylphosphine) chloro-rhodium in 6 ml of benzene and 15 ml of ethanol is stirred under hydrogen for 60 minutes. 6 Alpha,6 beta,9 alpha-trifluoro-11 beta-hydroxy-6 alpha-methyl-3-oxo-17 alpha-propionyloxyandrosta-1,4-diene 17 beta-carboxylic acid (244 mg) is added and the resulting solution is stirred under hydrogen at room temperature at atmospheric pressure. After hydrogen uptake is complete, the solution is evaporated to dryness and the residue taken up in a mixture of petroleum ether and methylene chloride. The pure product is isolated by column chromatography on silica gel to give 4,6 alpha,9 alpha-trifluoro-11 beta-hydroxy-16 alpha-methyl-3-oxo-17 alpha-propionyloxyandrost-4-ene 17 beta-carboxylic acid.

Similarly, by substituting other androsta-1,4-diene steroids for 6 alpha,6 beta,9 alpha-trifluoro-11 beta-hydroxy-16 alpha-methyl-3-oxo-17 alpha-propionylandrosta-1,4-diene 17 beta-carboxylic acid other corresponding androst-4-ene steroids are prepared. These are readily reacted according to the process of Examples 1 and 2 to form the 17 beta-thiocarboxylates of this invention.

What is claimed is:

1. A compund chosen from those represented by the formula

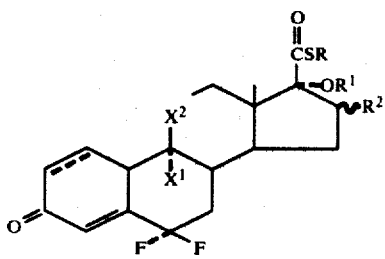

(I)

wherein
$X^1$ is hydrogen, fluoro, chloro or bromo;
$X^2$ is =C=O or

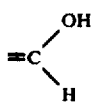

or is

when $X^1$ is chloro;
R is alkyl of 1 through 6 carbon atoms or phenyl or benzyl optionally substituted with one substituent on the phenyl ring chosen from the group consisting of alkyl of 1 through 4 carbon atoms, alkoxy of 1 through 4 carbon atoms and halo;
$R^1$ is hydrogen or alkanoyl of 2 through 6 carbon atoms when $R^2$ is hydrogen, alpha-methyl or beta-methyl;
$OR^1$ and $R^2$ together are 16 alpha,17 alpha-isopropylidenedioxy; and
the broken line between C-1 and C-2 represents a double or a single bond.

2. A compound of claim 1 wherein
$R^2$ is alpha-methyl;
$R^1$ is alkanoyl of 2 through 6 carbon atoms;
R is alkyl of 1 through 6 carbon atoms, benzyl or phenyl;
$X^1$ is hydrogen, fluoro or chloro; and
$X^2$ is

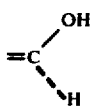

or is

when $X^1$ is chloro.

3. A compound of claim 2 wherein R is alkyl of 1 or 2 carbon atoms, $X^1$ is fluoro or chloro, and $X^2$ is

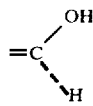

or is

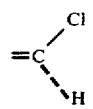

when $X^1$ is chloro.

4. A compound of claim 3 wherein $X^1$ is fluoro and $X^2$ is

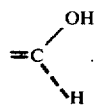

5. A compound of claim 4 wherein the bond between C-1 and C-2 is a double bond, R is methyl and $R^1$ is propionyl, namely methyl 6 alpha,6 beta,9 alpha-trifluoro-11 beta-hydroxy-16 alpha-methyl-3-oxo-17 alpha-propionyloxyandrosta-1,4-diene 17 beta-thiocarboxylate.

6. A compound of claim 5 wherein $X^1$ is chloro and $X^2$ is

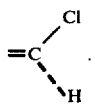

7. A compound of claim 6 wherein the bond between C-1 and C-2 is a double bond, R is methyl and $R^1$ is propionyl, namely methyl 9 alpha, 11 beta-dichloro-6 alpha, 6 beta-difluoro-16 alpha-methyl-3-oxo-propionyloxyandrosta-1,4-diene 17 beta-thiocarboxylate.

8. A compound of claim 1 wherein $X^1$ is hydrogen, fluoro or chloro; $X^2$ is

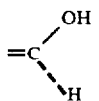

or is

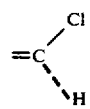

when $X^1$ is chloro; R is alkyl of 1 through 6 carbon atoms; and $OR^1$ and $R^2$ together are 16 alpha,17 alpha-isopropylidenedioxy.

9. A compound of claim 8 wherein R is methyl and $X^1$ is fluoro or chloro.

10. A compound of claim 9 wherein $X^1$ is fluoro, namely methyl 6 alpha,6 beta,9 alpha-trifluoro-11 beta-hydroxy-16 alpha,17 alpha-isopropylidenedioxy-3-oxoandrosta-1,4-diene 17 beta-thiocarboxylate.

11. A compound of claim 9 wherein $X^1$ is chloro and $X^2$ is

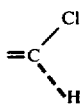

namely methyl 9 alpha,11 beta-dichloro-6 alpha,6 beta-difluoro-16 alpha,17 alpha isopropylidenedioxy-3-oxoandrosta-1,4-diene 17 beta-thiocarboxylate.

12. An anti-inflammatory pharmaceutical composition which comprises about 0.001% by weight to about 10% by weight of a compound of claim 1 in combination with about 90% by weight to about 99.999% by weight of suitable pharmaceutical excipients.

13. An anti-inflammatory pharmaceutical composition which comprises about 0.001% by weight to about 10% by weight of a compound of claim 2 in combination with about 0.001% by weight to about 10% by weight of suitable pharmaceutical excipients.

14. An anti-inflammatory pharmaceutical composition which comprises about 0.001% by weight to about 10% by weight of a compound of claim 3 in combination with about 0.001% by weight to about 10% by weight of suitable pharmaceutical excipients.

15. An anti-inflammatory pharmaceutical composition which comprises about 0.001% by weight to about 10% by weight of a compound of claim 8 in combination with about 0.001% by weight to about 10% by weight of suitable pharmaceutical excipients.

16. An anti-inflammatory pharmaceutical composition which comprises about 0.001% by weight to about 10% by weight of a compound of claim 8 in combination with about 0.001% by weight to about 10% by weight of suitable pharmaceutical excipients.

17. A process for relieving inflammatory manifestations of corticosteroid responsive dermatoses in a mammal which comprises administering a therapeutically effective amount of a compound of claim 1 to said mammal.

18. A process for relieving inflammatory manifestations of corticosteroid responsive dermatoses in a mammal which comprises administering a therapeutically effective amount of a compound of claim 2 to said mammal.

19. A process for relieving inflammatory manifestations of corticosteroid responsive dermatoses in a mammal which comprises administering a therapeutically effective amount of a compound of claim 3 to said mammal.

20. A process for relieving inflammatory manifestations of corticosteroid responsive dermatoses in a mammal which comprises administering a therapeutically effective amount of a compound of claim 8 to said mammal.

21. A process for relieving inflammatory manifestations of corticosteroid responsive dermatoses in a mammal which comprises administering a therapeutically effective amount of a compound of claim 9 to said mammal.

* * * * *